US008344076B2

(12) United States Patent
Dershem

(10) Patent No.: US 8,344,076 B2
(45) Date of Patent: Jan. 1, 2013

(54) HYDROLYTICALLY RESISTANT THERMOSET MONOMERS

(75) Inventor: Stephen M Dershem, San Diego, CA (US)

(73) Assignee: Designer Molecules, Inc., San Diego, CA (US)

( * ) Notice: Subject to any disclaimer, the term of this patent is extended or adjusted under 35 U.S.C. 154(b) by 942 days.

(21) Appl. No.: 11/960,612

(22) Filed: Dec. 19, 2007

(65) Prior Publication Data

US 2008/0142158 A1   Jun. 19, 2008

Related U.S. Application Data

(60) Provisional application No. 60/875,573, filed on Dec. 19, 2006.

(51) Int. Cl.
*B05D 3/02* (2006.01)
*C07C 69/734* (2006.01)
*C07C 69/75* (2006.01)
*C08G 59/16* (2006.01)
*C08L 33/14* (2006.01)
*C09J 4/00* (2006.01)
*C09J 133/14* (2006.01)

(52) U.S. Cl. ........ 525/531; 156/326; 156/332; 525/502; 528/106; 560/126; 560/181

(58) Field of Classification Search .................. None
See application file for complete search history.

(56) References Cited

U.S. PATENT DOCUMENTS

| 4,111,879 | A | 9/1978 | Mori et al. |
|---|---|---|---|
| 4,968,738 | A | 11/1990 | Dershem |
| 5,045,127 | A | 9/1991 | Dershem et al. |
| 5,064,480 | A | 11/1991 | Dershem et al. |
| 5,232,962 | A | 8/1993 | Dershem et al. |
| 5,306,333 | A | 4/1994 | Dershem et al. |
| 5,358,992 | A | 10/1994 | Dershem et al. |
| 5,403,389 | A | 4/1995 | Dershem |
| 5,447,988 | A | 9/1995 | Dershem et al. |
| 5,489,641 | A | 2/1996 | Dershem |
| 5,602,205 | A | 2/1997 | Singh et al. |
| 5,646,241 | A | 7/1997 | Dershem et al. |
| 5,714,086 | A | 2/1998 | Osuna et al. |
| 5,717,034 | A | 2/1998 | Dershem et al. |
| 5,718,941 | A | 2/1998 | Dershem et al. |
| 5,753,748 | A | 5/1998 | Dershem et al. |
| 5,861,111 | A | 1/1999 | Dershem et al. |
| 5,969,036 | A | 10/1999 | Dershem |
| 5,973,166 | A | 10/1999 | Mizori et al. |
| 6,034,150 | A | 3/2000 | Hoyle et al. |
| 6,034,194 | A | 3/2000 | Dershem |
| 6,034,195 | A | 3/2000 | Dershem |
| 6,048,953 | A | 4/2000 | Kawashimu et al. |
| 6,121,358 | A | 9/2000 | Dershem et al. |
| 6,153,794 | A * | 11/2000 | Funaki et al. .................. 564/14 |
| 6,187,886 | B1 | 2/2001 | Husson et al. |
| 6,211,320 | B1 | 4/2001 | Dershem et al. |
| 6,300,456 | B1 | 10/2001 | Musa |
| 6,369,124 | B1 | 4/2002 | Hoyle et al. |
| 6,423,780 | B1 | 7/2002 | Dershem et al. |
| 6,429,281 | B1 | 8/2002 | Dershem et al. |
| 6,521,731 | B2 | 2/2003 | Dershem et al. |
| 6,620,946 | B2 | 9/2003 | Dershem et al. |
| 6,743,852 | B2 | 6/2004 | Dershem et al. |
| 6,750,301 | B1 | 6/2004 | Bonneau et al. |
| 6,790,597 | B2 | 9/2004 | Dershem |
| 6,825,245 | B2 | 11/2004 | Dershem |
| 6,831,132 | B2 | 12/2004 | Liu et al. |
| 6,852,814 | B2 | 2/2005 | Dershem et al. |
| 6,855,745 | B2 | 2/2005 | Hoyle et al. |
| 6,916,856 | B2 | 7/2005 | Dershem |
| 6,946,523 | B2 | 9/2005 | Dershem et al. |
| 6,960,636 | B2 | 11/2005 | Dershem et al. |
| 6,963,001 | B2 | 11/2005 | Dershem et al. |
| 7,102,015 | B2 | 9/2006 | Dershem et al. |
| 7,157,587 | B2 | 1/2007 | Mizori et al. |
| 7,176,044 | B2 | 2/2007 | Forray et al. |
| 7,199,249 | B2 | 4/2007 | Liu et al. |
| 7,208,566 | B2 | 4/2007 | Mizori et al. |
| 7,285,613 | B2 | 10/2007 | Dershem et al. |
| 7,309,724 | B2 | 12/2007 | Dershem et al. |
| 7,517,925 | B2 | 4/2009 | Dershem et al. |
| 7,678,879 | B2 | 3/2010 | Dershem |
| 2002/0062923 | A1 | 5/2002 | Forray |
| 2002/0099168 | A1 | 7/2002 | Dershem et al. |
| 2002/0188137 | A1 | 12/2002 | Dershem et al. |

(Continued)

FOREIGN PATENT DOCUMENTS

EP          0393713          6/1994

(Continued)

OTHER PUBLICATIONS

NIshibuko et al., Study of Photopolymers. XXX. Syntheses of New Di(meth)acrylate Oligomers by Addition Reactions of Epoxy Compounds with Active Esters, Journal of Polymer Science; Part A: Polymer Chemistry, vol. 25, 1987, pp. 3049-3062.*
CAPLUS accession No. 2000:50077 for U.S. Patent No. 6,153,794, Funaki et al., Nov. 28, 2000 and registry No. 254897-21-7, three pages.*
Dalpozzo et al., "1,2-Diacetates by epoxide ring opening promoted by erbium (III) triflate," ARKIVOC, vol. 6, 2006, pp. 67-73.*
Dunbar et al., "The acylation of organic hydroxy compounds with ketene," Journal of Organic Chemistry, vol. 21, 1956, pp. 1041-1044 and HCPLUS accession No. 1958:10936, two pages.*
Kingsbury et al., "Conformation of Vicinal Diesters," Journal of Organic Chemistry, vol. 40, No. 9, 1975, pp. 1302-1308.*

(Continued)

*Primary Examiner* — Robert Sellers
(74) *Attorney, Agent, or Firm* — The Law Office of Jane K. Babin, Professional Corporation; Jane K. Babin

(57) ABSTRACT

The present invention provides hydrolytically resistant monomers prepared by the reaction of an epoxy compound and a reactive ester and methods for producing the monomers. Also provided are adhesive compositions containing the hydrolytically resistant monomers and methods for use thereof.

24 Claims, No Drawings

U.S. PATENT DOCUMENTS

| | | |
|---|---|---|
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |
| 2003/0060531 A1 | 3/2003 | Dershem et al. |
| 2003/0087999 A1 | 5/2003 | Dershem et al. |
| 2003/0096123 A1 | 5/2003 | Yeager |
| 2003/0109666 A1 | 6/2003 | Dershem et al. |
| 2003/0125551 A1 | 7/2003 | Dershem et al. |
| 2003/0199638 A1 | 10/2003 | Liu et al. |
| 2003/0208016 A1 | 11/2003 | Dershem et al. |
| 2004/0006166 A1 | 1/2004 | Liu et al. |
| 2004/0019224 A1 | 1/2004 | Dershem et al. |
| 2004/0077798 A1 | 4/2004 | Dershem et al. |
| 2004/0082724 A1 | 4/2004 | Dershem et al. |
| 2004/0102566 A1 | 5/2004 | Forray et al. |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0107542 A1 | 5/2005 | Liu et al. |
| 2005/0136620 A1 | 6/2005 | Dershem et al. |
| 2005/0137277 A1 | 6/2005 | Dershem et al. |
| 2005/0267254 A1 | 12/2005 | Mizori et al. |
| 2005/0272888 A1 | 12/2005 | Dershem et al. |
| 2006/0009570 A1 | 1/2006 | Zychowski |
| 2006/0009578 A1 | 1/2006 | Dershem |
| 2006/0063014 A1 | 3/2006 | Forray |
| 2006/0069232 A1 | 3/2006 | Dershem |
| 2006/0116476 A1 | 6/2006 | Cheng |
| 2006/0142517 A1 | 6/2006 | Dershem |
| 2007/0078198 A1* | 4/2007 | Otsuji et al. ................. 523/120 |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dersham |
| 2008/0257493 A1 | 10/2008 | Dershem |
| 2008/0262191 A1 | 10/2008 | Mizori |
| 2008/0318188 A1* | 12/2008 | Stansbury et al. ............ 433/215 |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041823 A1 | 2/2010 | Dershem |
| 2010/0041832 A1 | 2/2010 | Dershem |
| 2010/0041845 A1 | 2/2010 | Dershem et al. |
| 2010/0056671 A1 | 3/2010 | Dershem |
| 2010/0063184 A1 | 3/2010 | Dershem |

FOREIGN PATENT DOCUMENTS

| | | |
|---|---|---|
| EP | 1156036 | 11/2001 |
| WO | WO-2005121190 | 12/2005 |
| WO | WO-2007100329 | 9/2007 |
| WO | WO-2008077141 | 6/2008 |
| WO | WO-2008124797 | 10/2008 |
| WO | WO-2008130894 | 10/2008 |
| WO | WO-2010019832 | 2/2010 |

OTHER PUBLICATIONS

Nazarov et al. HCAPLUS accession No. 1957:51676, Synthesis of dienes with fixed trans configuration of dobuld bonds. 3-methylencyclohexene, Doklady Akademii Nauk SSSR, vol. 111, 1956, two pages.*

HCAPLUS accession No. 1999:672355 for European Patent No. 950,649 A1, Nobori et al., Oct. 20, 1999, two pages.*

Anand et al., "Copolymerization and thermal behavior of methyl methacrylate with N-(phenyl/p-tolyl) itaconimides", *Journal of Applied Polymer Science 89*: 2003, 1195-1202.

Andersson et al., "Initiator-Free Photopolymerization of an Aliphatic Vinyl Ether-Maleimide Monomer", *J Coatings Tech 69*: 1997, 91-95.

Grenier-Loustalot et al., "Monofunctional maleimide or acetylene tennlnated model compounds—I. Molten state homopolymerization reactivity and kinetics", *European Polymer Journal 34*: 1998, 1705-1714.

Kohli et al., "Co-Polymerization of Maleimides and Vinyl Ethers: A Structural Study", *Macromolecules 31*: 1998, 5681-5689.

Yamazaki et al., "Effect of N-substrtuents on polymerization reactivity of N-alkylitaconimides in radical polymerization", *European Polymer Journal 33*: 1997, 157-162.

* cited by examiner

HYDROLYTICALLY RESISTANT THERMOSET MONOMERS

RELATED APPLICATIONS

This application claims the benefit of priority under 35 USC §119 of U.S. Provisional Application Ser. No. 60/875,573 filed Dec. 19, 2006, the entire disclosure of which is incorporated herein by reference.

FIELD OF THE INVENTION

The present invention relates generally to thermoset monomers, thermosetting adhesive compositions containing these monomers, methods of preparation and uses therefor. In particular, the present invention relates to thermosetting compounds and compositions containing secondary alcohol esters of acrylic and methacrylic acid as well as styrenyl functional monomers.

BACKGROUND OF THE INVENTION

Thermoset monomers are used to make commercially useful articles. They are also used in a variety of adhesive compositions. Monomers used in these applications include acrylate, methacrylate, fumarate, maleate, maleimide, and stryenic functional compounds. Resistance to hydrolytic degradation of the adhesive bonds formed from these thermoset adhesives is often a critical performance requirement. The performance of these adhesives, in the presence of hot and wet environments, is directly connected to the hydrolytic resistance of the chemical linkages within the monomers themselves.

There remains a need to produce hydrolytically stable, free radically polymerizable monomers to meet the increasing demands of the electronics and other industries.

It is well known in the art, that the esters of secondary alcohols are significantly more resistant to hydrolysis than esters of primary alcohols. Nevertheless, few radically polymerizable thermoset monomers containing these desirable secondary alcohol ester linkages have been developed despite a clear need for such compounds and their potential widespread application. The only readily available monomers in this class include isobornyl acrylate, isobornyl methacrylate, 3,3,5-trimethylcyclohexyl methacrylate, and cyclohexyl methacrylate. Thus, although such alcohols have the potential for filling the need for hydrolytic stability, the paucity of monomers having the above-mentioned characteristics limits their current potential in the adhesives and other industries.

There remains a need to produce hydrolytically stable, free radically polymerizable monomers to meet the increasing demands of the electronics and other industries.

SUMMARY OF THE INVENTION

The present invention provides compounds having the formula:

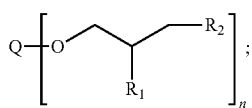
(I)

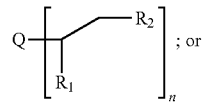
(II)

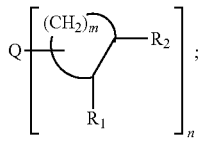
(III)

where $R_1$ and $R_2$ are each independently substituted or unsubstituted acyloxy, cycloacyloxyl, benzoxy, acryloxy, methacryloxy, maleimido acyloxy, styryloxy, cinnamyloxy, 2,2,2-trifluoroethoxy, 2-nitroethoxy, 2-cyanoethoxy, acetomethoxy, or aryloxy; Q is a single unit, or a repeat unit within a polymer backbone, that is a substituted or unsustituted alkly, cycloalkyl, aryl, or heterocyclic hydrocarbon having from 2 to about 100 carbon atoms; m is 3 to 10; and n is 1 to about 11.

In certain embodiments of the invention, The compound of claim 1 wherein at least one of $R_1$ or $R_2$ is selected from

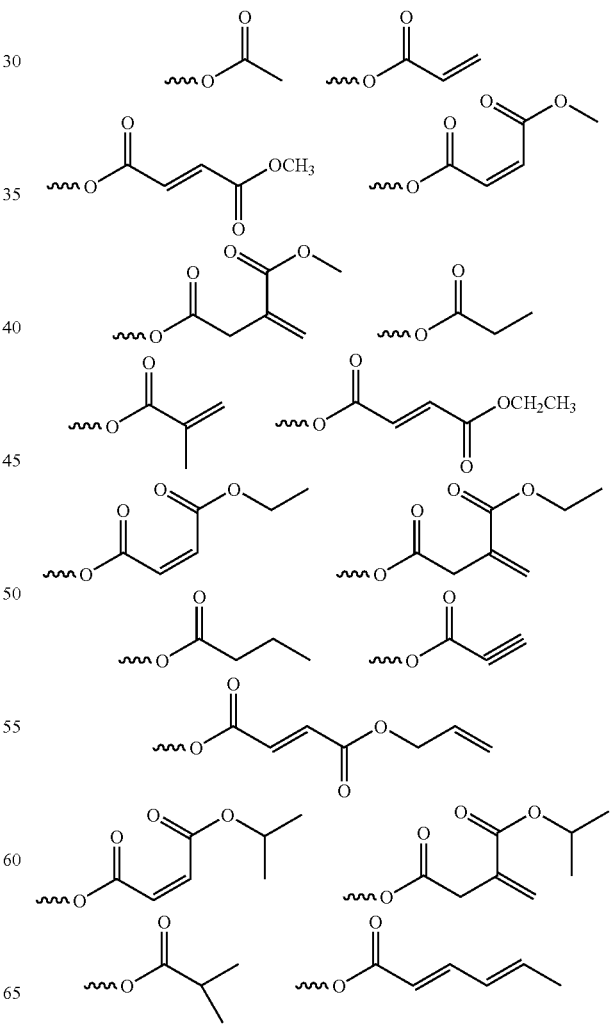

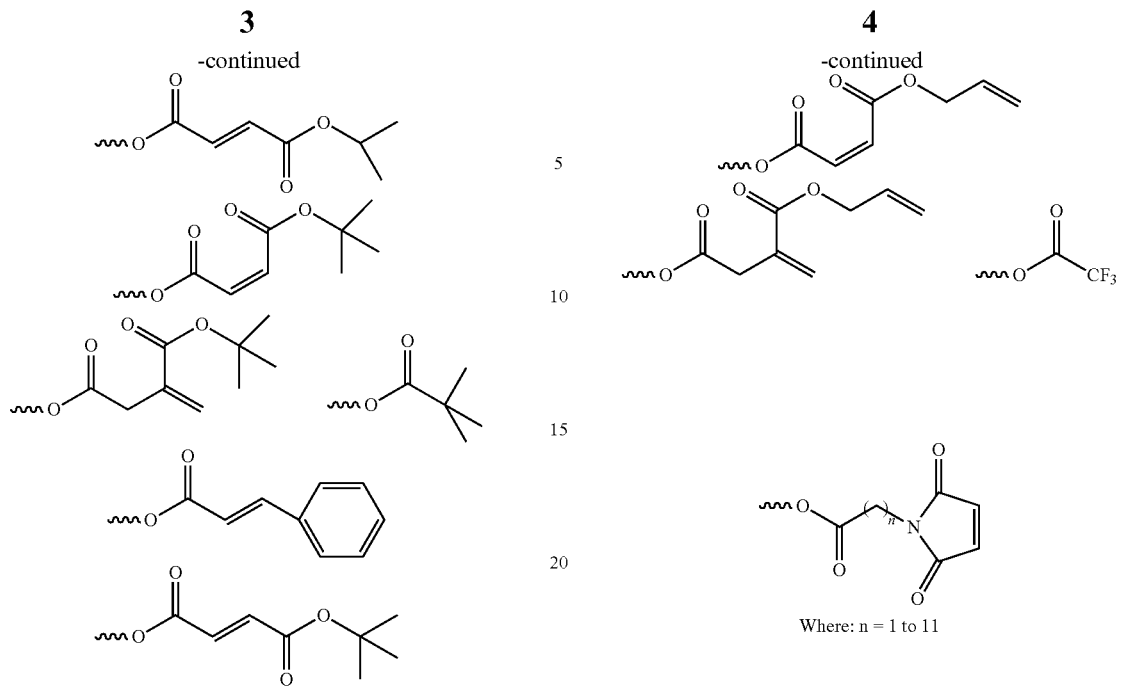
Exemplary compounds of the invention include:
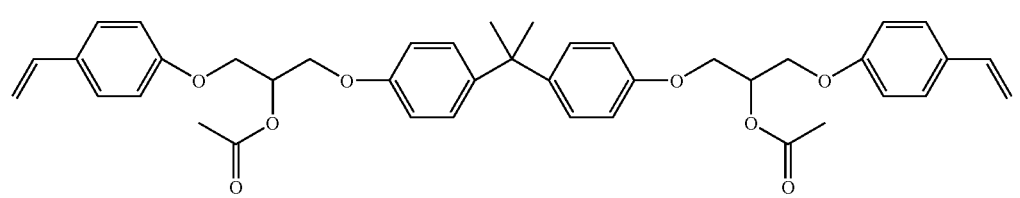
C-1
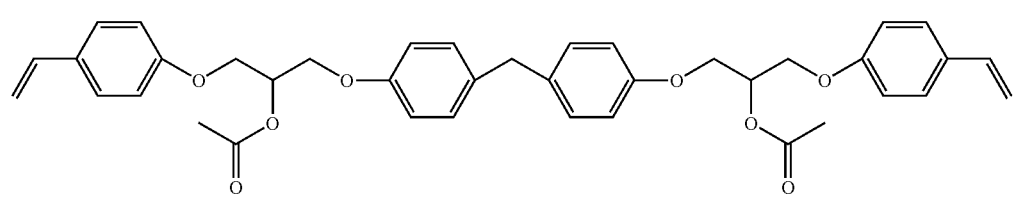
C-2
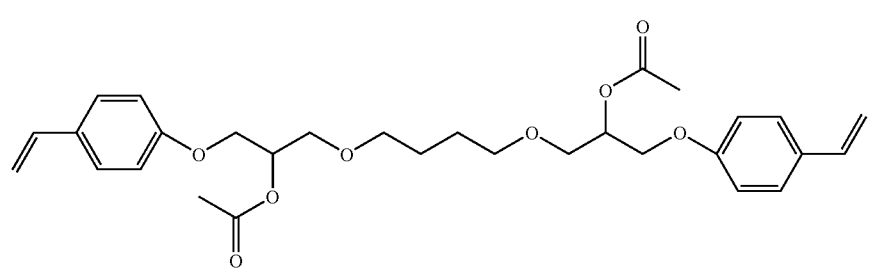
C-3
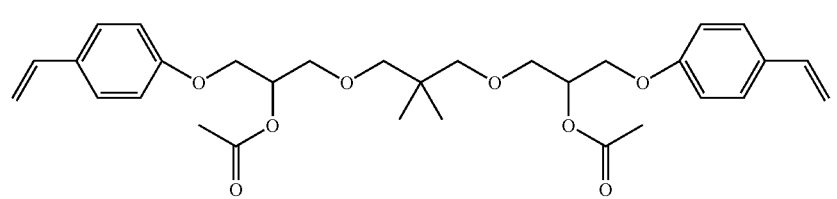
C-4

-continued
C-5
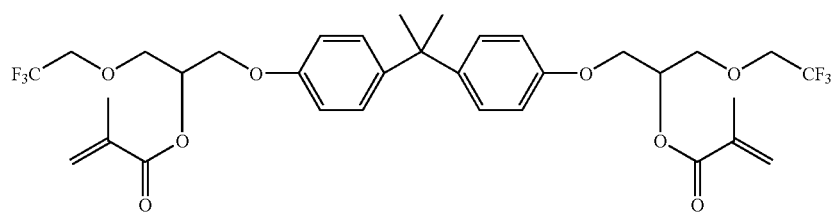
C-6
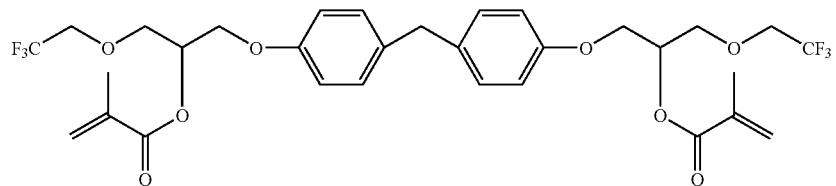
C-7
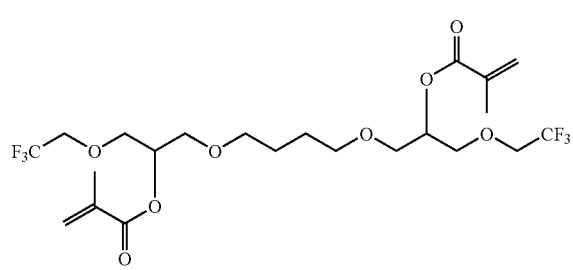
C-8
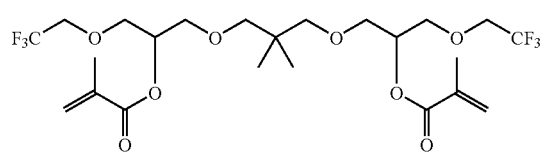
C-9
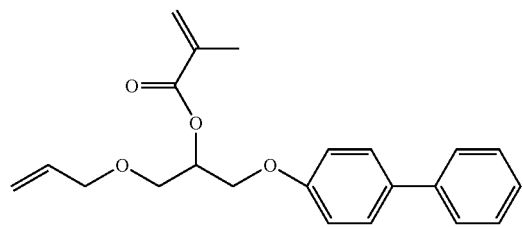
C-10
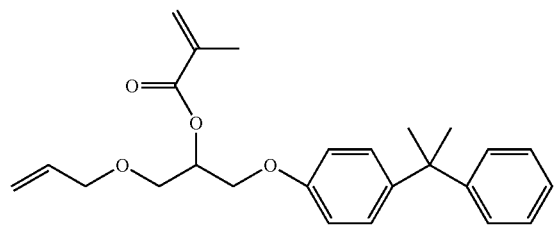
C-11
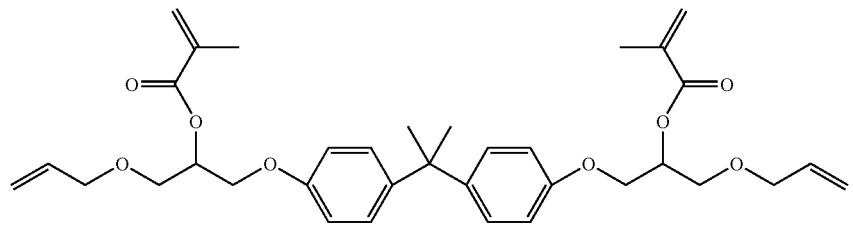
C-12
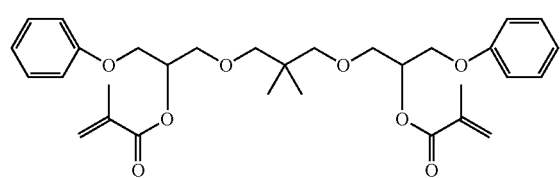
C-13
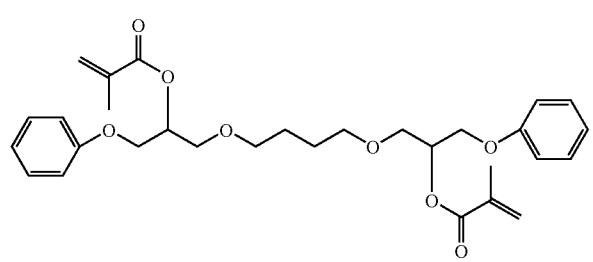

-continued

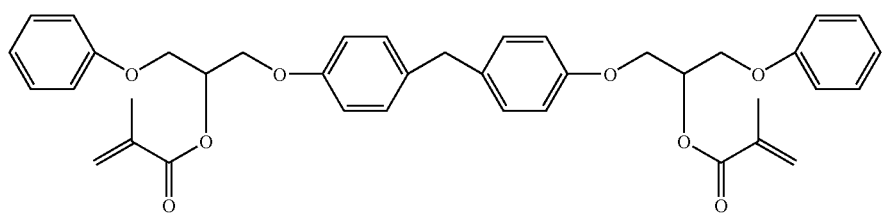
C-14

C-15   C-16

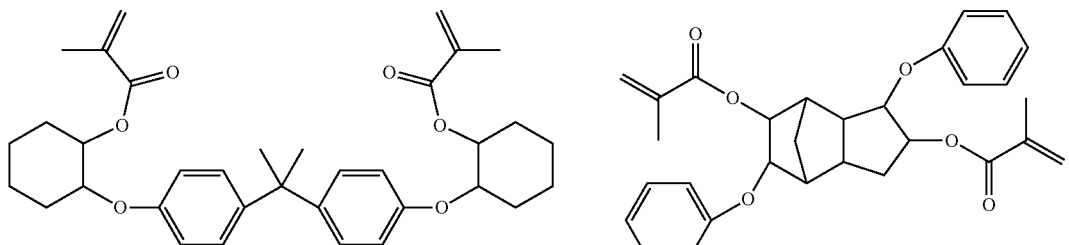
C-17   C-18

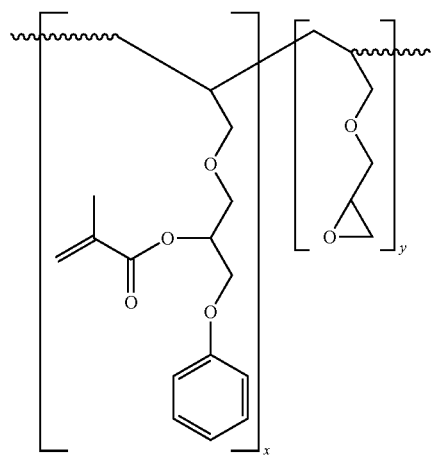
C-19

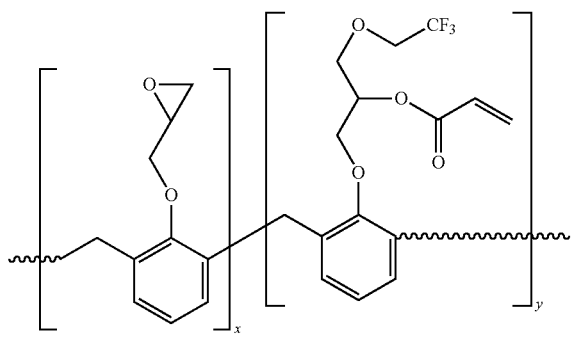
C-20 where x and y are independently about 1 to about 10.

Also provided by the present invention are methods for preparing the compound of formula I, II and II by contacting an epoxy with a reactive ester in the presence of a catalyst, where a free radical curable monomer is produced, and thereby preparing the compound. In certain embodiments, the epoxy is only partially converted to a free radical polymerizable moiety, while in other embodiments, the epoxy is fully converted.

The catalyst is typically a basic catalyst, such as 4-(N,N-dimethylamino)pyridine (DMAP), 4-(4-methyl-1-piperidinyl)pyridine (MPP), 1,5-diazabicyclo[4.3.0]non-5-ene (DBN), 1,4-diazabicyclo[2.2.2]octane (DABCO), 1,8-diazabicyclo[5.4.0]undec-7-ene (DBU), or tetrabutylammonium bromide (TBAB).

The epoxy is can be a mono-, bi-functional, or poly-functional glycidyl ether epoxy, cycloaliphatic epoxy or aliphatic epoxy, including, but not limited to: a phenyl glycidyl ether; a cresyl glycidyl ether; a nonylphenyl glycidyl ether; a p-tert-butylphenyl glycidyl ether; triglycidyl-p-aminophenol, N,N,N',N'-tetraglycidyl-4,4'-diphenylmethane, triglycidyl isocyanurate, bis(4-hydroxyphenyl)sulfone, bis(hydroxyphenyl) sulfide, 1,1-bis(hydroxyphenyl)cyclohexane, 9,19-bis(4-hydroxyphenyl)fluorene, 1,1,1-tris(hydroxyphenyl)ethane, tetrakis(4-hydroxyphenyl)ethane, trihydroxytritylmethane, 4,4'-(1-alpha-methylbenzylidene) bisphenol, 4,4'-dihyroxy-benzophenone, resorcinol, catechol, or tetrahydroxydiphenyl sulfide; a glycidyl ether of a cresol formaldehyde condensate; a glycidyl ether of a phenol formaldehyde condensate; a glycidyl ether of a cresol dicyclopentadiene addition compound; a glycidyl ether of a phenol dicyclopentadiene addition compound; a glycidyl ether of dihydroxy naphthalene, 2,2'-dihydroxy-6,6'-dinaphthyl disulfide, or 1,8,9-trihydroxyanthracene; a diglycidyl ether of 1,4 butanediol; a diglycidyl ether of diethylene glycol; a diglycidyl ether of neopentyl glycol; a diglycidyl ether of cyclohexane dimethanol; a diglycidyl ether of tricyclodecane dimethanol; a trimethyolethane triglycidyl ether; a trimethyol propane triglycidyl ether; a glycidyl ether of a polyglycol; a polyglycidyl ether of castor oil; a polyoxypropylene diglycidyl ether; or a glycidyl derivative of an aromatic amine; cyclohexene oxide; 3-vinylcyclohexene oxide; vinylcyclohexene dioxide; dicylcopentadiene dioxide; tricyclopentadiene dioxide; tetracyclopentadiene dioxide; norbornadiene dioxide; bis(2,3-epoxycyclopentyl)ether; limonene dioxide; 3',4'-epoxycyclohexamethyl-3,4-epoxycyclohexanecarboxylate; 3,4-epoxycyclohexyloxirane; 2(3',4'-epoxycyclohexyl)-5,1"-spiro-3",4"-epoxycyclohexane-1,3-dioxane; or bis(3,4-epoxycyclohexamethyl)adipate; epoxidized polybutadiene; epoxidized polyisoprene; epoxidized poly(1,3-butadiene-acrylonitrile); epoxized soybean oil; epoxidized castor oil; dimethylpentane dioxide; divinylbenzene dioxide; butadiene dioxide; or 1,7-octadiene dioxide.

In certain embodiments of methods of the invention, the reactive ester is a carboxylic acid ester of a substituted or unsubstituted phenols; a perfluorocarbon substituted methanol; a 2-cyanoethanol; a 2-nitroethanol; or acetol.

The invention further provides adhesive compositions containing at least one compound of formula I, II and/or II, and at least one curing initiator. Such compositions may, for example, contain 0.05 weight percent to about 98 weight percent of a monomer compound at least one compound of formula I, II and/or II; optionally 0.05 weight percent to about 98 weight percent of at least one co-monomer; and 0.1 weight percent to about 5 weight percent of a curing initiator.

The curing initiator is typically a free-radical initiator or a photoinitiator such as dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis (tert-butyl peroxyisopropyl)benzene, tert-butyl hydroperoxide), 2,2'-azobis(2-methyl-propanenitrile), 2,2'-azobis(2-methylbutanenitrile), a 1,1'-azobis(cyclohexanecarbonitrile), a benzoin derivative, a benzilketal, an α,α-dialkoxyacetophenone, an α-hydroxyalkylphenone, an α-aminoalkylphenone, an acylphosphine oxide, a titanocene compound, a benzophenone, an amine, Michler's ketone. Curing initiators containing a combination of a free-radical initiator and a photoinitiator are also encompassed by the invention.

The comonomer, when present, can be an acrylate, a methacrylate, a maleimide, a vinyl ether, a vinyl ester, a styrenic compound, an allyl functional compound, an olefin, an epoxy, an oxetane, a benzoxazine, an anhydride, a phenyl ester, and a phenol.

The adhesive compositions of the invention are useful in invention methods for adhesively attaching a first article to a second article by applying an aliquot of the adhesive composition to the first article, the second article or both the first article and the second article; bringing the first article and the second article into intimate contact to form an assembly wherein the first article and the second article are separated only by the adhesive composition; and curing the adhesive composition.

The present invention also provides adhesive compositions containing a monomer of formula I, II and/or II in which the epoxy is only partially converted to a free radical polymerizable moiety, optionally a comonomer, and a curing initiator. Such partially cured adhesive compositions are particularly useful in staged methods for adhesively attaching a first article to a second article by applying an aliquot of the adhesive composition to the first article, the second article or both the first article and the second article; bringing the first article and the second article into intimate contact to form an assembly wherein the first article and the second article are separated only by the adhesive composition; curing either an epoxy or free-radical moiety of the monomer, thereby producing a cured moiety and an uncured moiety of the adhesive composition; and thereafter curing the remaining uncured moiety.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

The present invention is based on the discovery of a new class of hydrolytically resistant monomers prepared by the reaction of an epoxy compound and a reactive ester. The monomers compounds of the invention, and compositions containing these monomers, have the properties of hydrophobicity, hydrolytic stability, and low cure stress that make them useful as adhesives for the electronic packaging industry as well as in a in a variety of other applications.

Among the many applications for the compounds and compositions of the invention are automotive, marine, and aerospace coatings, resins, and adhesives; dental matrix resins and adhesives; as components of matrix resins for composites used in sports equipment, automotive bodies, and boat construction; as well as use in adhesives for diverse industrial applications such as thread-lock materials and building materials.

The present invention provides compounds that are free-radically polymerizable monomers containing secondary alcohol ester linkages. Such hydrolytically resistant monomers can be prepared by the reaction of an epoxy compound and a reactive ester. A multitude of epoxy compounds and reactive esters are available, which can be combined according to the present invention to yield a wide variety of mono- and multi-functional, free radically polymerizable monomers that have not heretofore been described.

The present invention also provides methods for preparing free radically polymerizable monomers containing secondary alcohol ester linkages, by reacting an epoxy compound with a reactive ester. These compounds may be prepared in the presence of a basic catalyst, examples of which include, 4-(N,N-dimethylamino)pyridine (DMAP); 4-(4-methyl-1-piperidinyl)pyridine (MPP); 1,5-diazabicyclo[4.3.0]non-5-ene (DBN); 1,4-diazabicyclo[2.2.2]octane (DABCO); 1,8-diazabicyclo[5.4.0]undec-7-ene (DBU);

tetrabutylammonium bromide (TBAB); and the like. Thus, in one embodiment of the invention, the method includes by reacting an epoxy compound with a reactive ester in the presence of a basic catalyst.

The epoxy compound may itself be mono or polyfunctional. The epoxy compound may also be a glycidyl ether, aliphatic, or cycloaliphatic epoxy.

The reactive esters include carboxylic acid esters of substituted or unsubstituted phenols, perfluorocarbon substituted methanol, 2-cyanoethanol, 2-nitroethanol, and acetol. All of the phenols and each of the alcohols bearing electron withdrawing substitutents are themselves weakly acidic. This property makes their corresponding esters more reactive than the esters of ordinary aliphatic alcohols.

The present invention also provides compound having the structure set forth in formula I, II, or III below. The reaction product of a glycidyl ether epoxy and a reactive ester according to the present invention, is represented by formula (I):

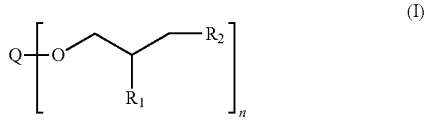
(I)

wherein:
- $R_1$ and $R_2$ are each independently substituted or unsubstituted acyloxy, cycloacyloxyl, benzoxy, acryloxy, methacryloxy, maleimido acyloxy, styryloxy, cinnamyloxy, 2,2,2-trifluoroethoxy, 2-nitroethoxy, 2-cyanoethoxy, acetomethoxy, or aryloxy;
- Q is a single unit, or a repeat unit within a polymer backbone, that is a substituted or unsustituted alkly, cycloalkyl, aryl, or heterocyclic hydrocarbon having from 2 to about 100 carbon atoms; and
- n is 1 to about 11.

The reaction product of an aliphatic epoxy and a reactive ester according to the present invention, is represented by formula (II):

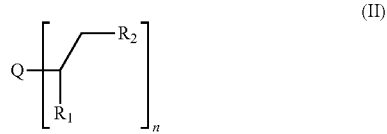
(II)

wherein:
- $R_1$ and $R_2$ are each independently substituted or unsubstituted acyloxy, cycloacyloxyl, benzoxy, acryloxy, methacryloxy, maleimido acyloxy, styryloxy, cinnamyloxy, 2,2,2-trifluoroethoxy, 2-nitroethoxy, 2-cyanoethoxy, acetomethoxy, or aryloxy;
- Q is a single unit, or a repeat unit within a polymer backbone, that is a substituted or unsustituted alkly, cycloalkyl, aryl, or heterocyclic hydrocarbon having from 2 to about 100 carbon atoms; and
- n is 1 to about 11.

The reaction product of a cycloaliphatic epoxy and a reactive ester according to the present invention, is represented by formula (III):

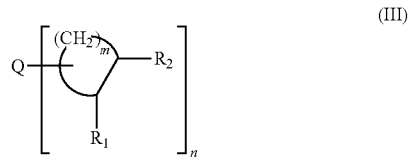
(III)

wherein:
- $R_1$ and $R_2$ are each independently substituted or unsubstituted acyloxy, cycloacyloxyl, benzoxy, acryloxy, methacryloxy, maleimido acyloxy, styryloxy, cinnamyloxy, 2,2,2-trifluoroethoxy, 2-nitroethoxy, 2-cyanoethoxy, acetomethoxy, or aryloxy;
- Q is a single unit, or a repeat unit within a polymer backbone, that is a substituted or unsustituted alkly, cycloalkyl, aryl, or heterocyclic hydrocarbon having from 2 to about 100 carbon atoms;
- m is 3 to 10;
- and
- n is 1 to about 11.

The skilled artisan will recognize that the styrenyl functional monomer compounds of the invention are unique in that it is the phenolic portion of the reactive ester, not the acyloxy substituent, which imparts polymerizability to the final adhesives. This class of thermosets therefore has an even greater resistance to hydrolysis, because the continuous chain in the cured matrix contains only ether linkages, while the secondary ester linkage is merely pendant off of this continuous backbone.

As used herein, "alkyl" refers to straight or branched chain hydrocarbyl groups having from 1 up to about 500 carbon atoms. Whenever it appears herein, a numerical range, such as "1 to 500" or "$C_1$-$C_{500}$", refers to each integer in the given range; e.g., "$C_1$-$C_{500}$ alkyl" means that an alkyl group may comprise only 1 carbon atom, 2 carbon atoms, 3 carbon atoms, etc., up to and including 500 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—, —C(O)O—, —S—, —SO$_2$—, —OC(O)—O—, —NR—C(O)—, —NR—C(O)—NR—, —OC(O)—NR—, wherein R is H or lower alkyl, acyl, oxyacyl, carboxyl, carbamate, sulfonyl, sulfonamide, sulfuryl, and the like. As used herein, "lower alkyl" refers to alkyl moieties having from 1 to about 12 carbon atoms.

As used herein, "alkenyl" refers to straight or branched chain hydrocarbyl groups having at least one carbon-carbon double bond, and having in the range of about 2 up to about 500 carbon atoms, and "substituted alkenyl" refers to alkenyl groups further bearing one or more substituents as set forth above. As used herein, "lower alkenyl" refers to alkenyl moieties having from 2 to about 12 carbon atoms.

As used herein, "cycloalkyl" refers to cyclic ring-containing groups typically containing in the range of about 3 up to about 20 carbon atoms, and "substituted cycloalkyl" refers to cycloalkyl groups further bearing one or more substituents as set forth above.

As used herein, "aryl" refers to aromatic groups having in the range of 6 up to 20 carbon atoms and "substituted aryl" refers to aryl groups further bearing one or more substituents as set forth above.

As used herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above. The term heterocyclic is also intended to refer to heteroaromatic moieties.

The —$R_1$ or —$R_2$ moieties in formulas I, II, and III can be varied considerably in the practice of the invention. Exemplary acyloxy moieties are set forth below:

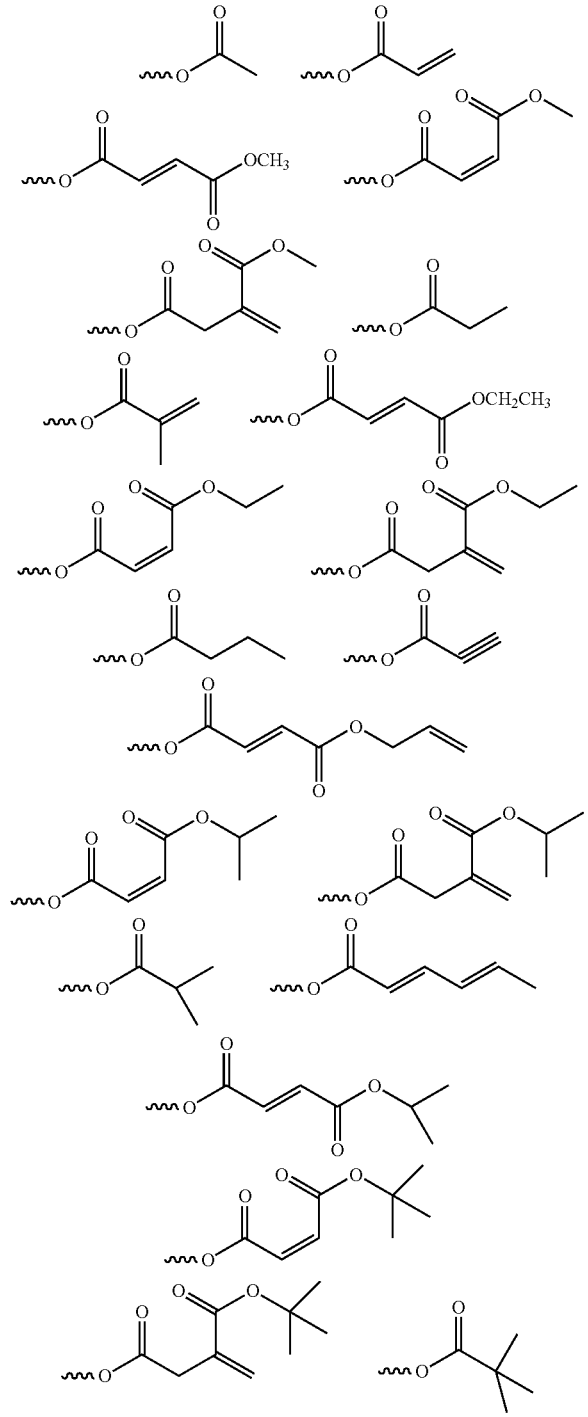

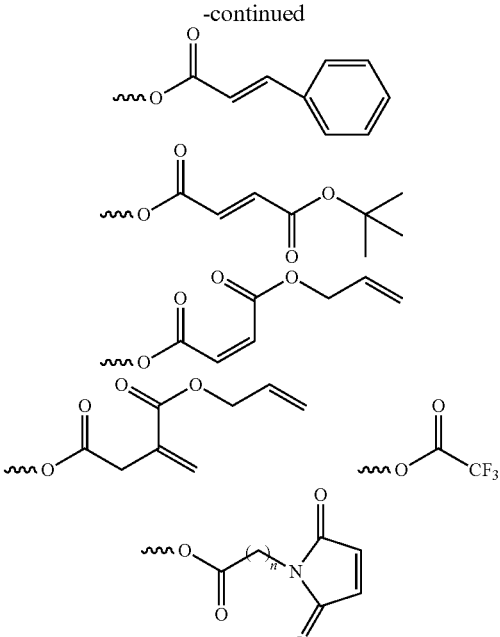

Where: n = 1 to 11

The acyloxy synthetic intermediates described in this invention are, in some cases, already commercially available. Phenyl methacrylate, bisphenol A dimethacrylate, and 4-acetoxystyrene, for example, are all commercially available. Those that are not available can be made by a variety of methods known in the art. The acyloxy compounds may be conveniently made via the reaction of a phenol or alcohol and a carboxylic acid anhydride. They may also be made through the reaction of a phenol or alcohol and an acid halide, preferably in the presence of a tertiary amine. These compounds can also be prepared by the direct condensation of a phenol or alcohol and an acid in the presence of a dehydrating agent such as 1,3-dicyclohexylcarbodiimide.

Glycidyl ether epoxy resins contemplated for use in the practice of the invention include, but are not limited to, glycidyl ether of a phenol, an amine, an alcohol, or an isocyanurate, selected from a phenyl glycidyl ether, a cresyl glycidyl ether, a nonylphenyl glycidyl ether, or a p-tert-butylphenyl glycidyl ether, a diglycidyl ether or a trisglycidyl ether of a phenolic compound selected from bisphenol A, bisphenol F, ethylidenebisphenol, dihydroxydiphenyl ether, triglycidyl-p-aminophenol, N,N,N',N'-tetraglycidyl-4,4'-diphenylmethane, triglycidyl isocyanurate, bis(4-hydroxyphenyl)sulfone, bis(hydroxyphenyl)sulfide, 1,1-bis(hydroxyphenyl)cyclohexane, 9,19-bis(4-hydroxyphenyl)fluorene, 1,1,1-tris(hydroxyphenyl)ethane, tetrakis(4-hydroxyphenyl)ethane, trihydroxytritylmethane, 4,4'-(1-alpha- methylbenzylidene) bisphenol, 4,4'-dihyroxybenzophenone, resorcinol, catechol, or tetrahydroxydiphenyl sulfide, a glycidyl ether of a cresol formaldehyde condensate, a glycidyl ether of a phenol formaldehyde condensate, a glycidyl ether of a cresol dicyclopentadiene addition compound, a glycidyl ether of a phenol dicyclopentadiene addition compound, a glycidyl ether of a fused ring polyaromatic phenol selected from dihydroxy naphthalene, 2,2'-dihydroxy-6,6'-dinaphthyl disulfide, or 1,8,9-trihydroxyanthracene, diglycidyl ether, a glycidyl ether of an aliphatic alcohol selected from a diglycidyl ether of 1,4 butanediol, a diglycidyl ether of diethylene glycol, a diglycidyl ether of neopentyl glycol, a diglycidyl ether of cyclohexane dimethanol, a diglycidyl ether of tricyclodecane dimethanol, a trimethyolethane triglycidyl ether, or a trimethyol propane triglycidyl ether, a glycidyl ether of a polyglycol selected from Heloxy 84™, Heloxy 32™, a polyglycidyl ether of castor oil, or a polyoxypropylene diglycidyl ether, a glycidyl derivative of an aromatic amine, ester linked epoxies, such as Heloxy 71, glycidylmethacrylate, and the like. Other glycidyl ether epoxies contemplated here include homo- and co-polymers based on allyl glycidyl ether.

Cycloaliphatic epoxy compounds contemplated for use in the practice of the invention include, but are not limited to, cyclohexene oxide; 3-vinylcyclohexene oxide; vinylcyclohexene dioxide; dicylcopentadiene dioxide; tricyclopentadiene dioxide; tetracyclopentadiene dioxide; norbornadiene dioxide; bis(2,3-epoxycyclopentyl)ether; limonene dioxide; 3',4'-epoxycyclohexamethyl-3,4-epoxycyclohexanecarboxylate; 3,4-epoxycyclohexyloxirane; 2(3',4'-epoxycyclohexyl)-5,1"-spiro-3",4"-epoxycyclohexane-1,3-dioxane; bis (3,4-epoxycyclohexamethyl)adipate; and the like.

Aliphatic epoxy compounds contemplated for use in the practice of the invention include, but are not limited to, epoxidized polybutadiene, epoxidized polyisoprene, epoxidized poly(1,3-butadiene-acrylonitrile), epoxized soybean oil, epoxidized castor oil, dimethylpentane dioxide, divinylbenzene dioxide, butadiene dioxide, 1,7-octadiene dioxide, and the like.

Exemplary difunctional monomers of the invention, where the epoxy compound starting materials is a difunctional glycidyl ether epoxy and the reactive ester used is 4-acetoxystyrene, are shown below as C-1 through C-4.

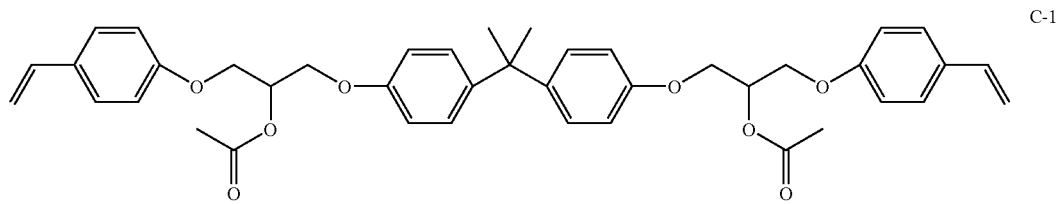

C-1

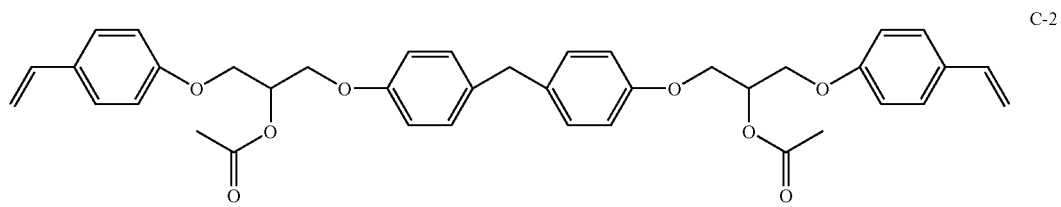

C-2

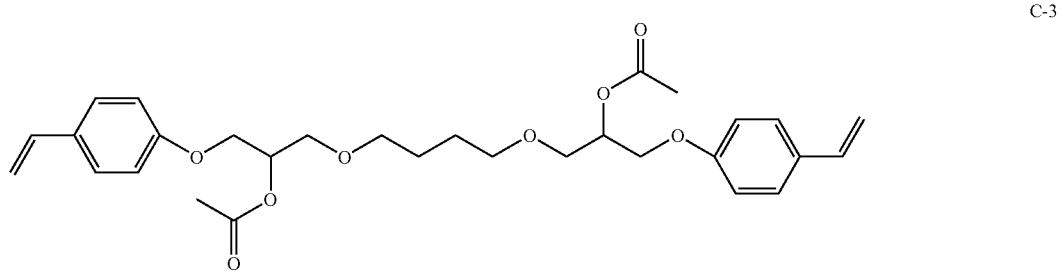

C-3

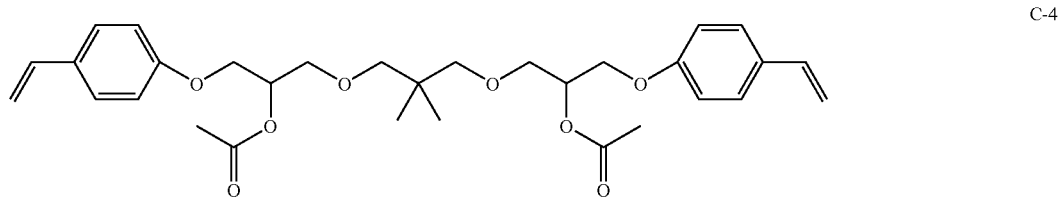

C-4

Exemplary difunctional monomers of the invention, where the epoxy compound starting material is a difunctional glycidyl ether epoxy and the reactive ester used is 2,2,2-trifluoroethyl methacrylate, are shown below as C-5 through C-8.

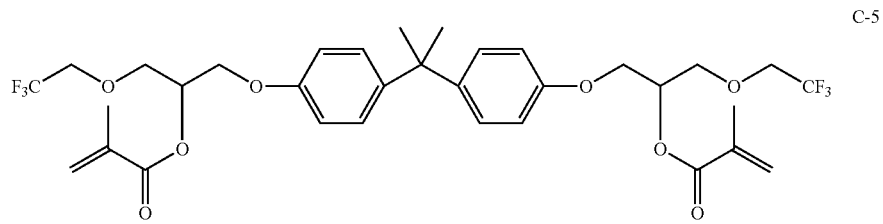

C-5

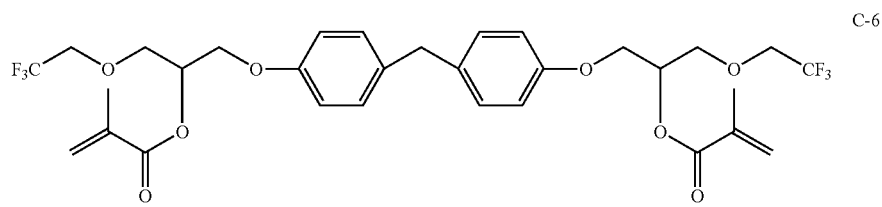

C-6

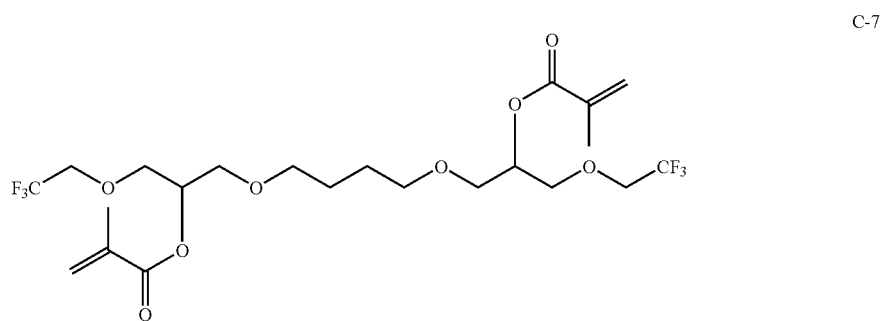

C-7

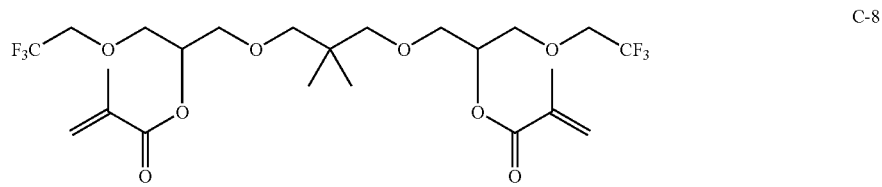

C-8

Exemplary multi-functional monomers of the invention, where the epoxy compound starting material is allyl glycidyl ether and the reactive ester used is a substituted phenyl or bisphenyl methacrylate compound, are shown below as C-9 through C-11.

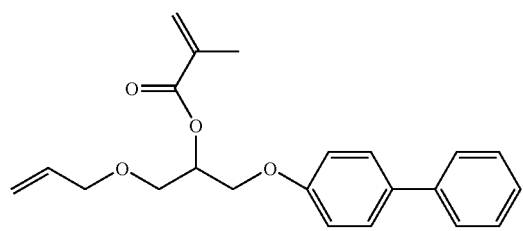

C-9

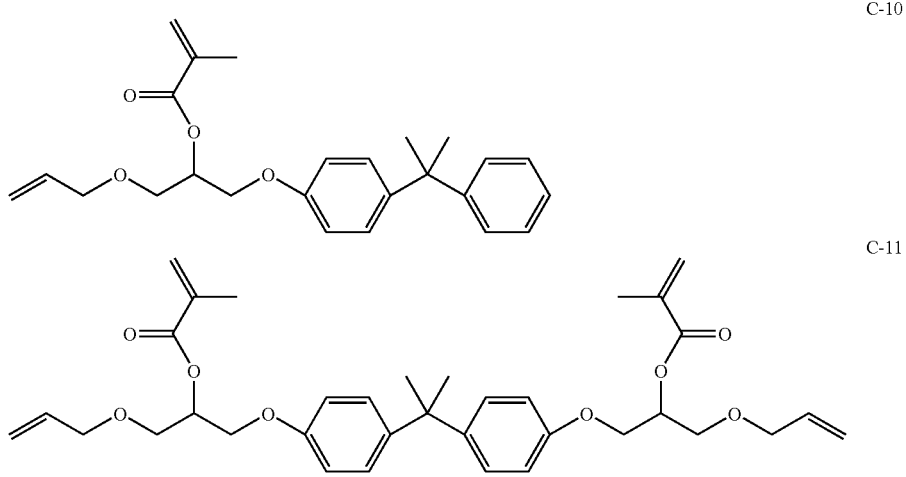

C-10

C-11

Exemplary difunctional monomers of the invention, where the epoxy compound starting material is a diglycidyl ether and the reactive ester used is phenyl methacrylate, are shown below as C-12 through C-14.

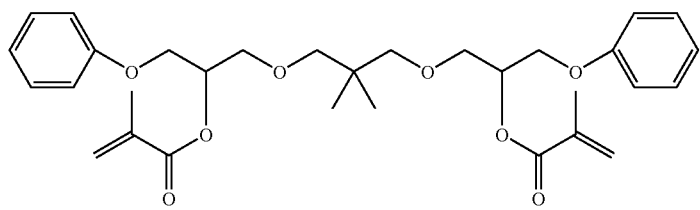

C-12

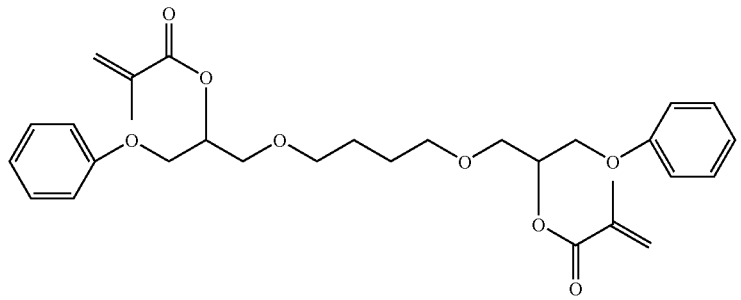

C-13

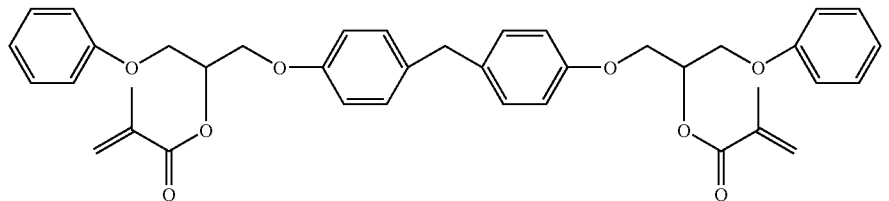

C-14

Exemplary mono and difunctional monomers of the invention, where the epoxy compound starting material is a cycloaliphatic epoxy and the reactive ester used is phenyl methacrylate, a substituted phenyl methacrylate, or bisphenol A dimethacrylate, are shown below as C-15 through C-18.

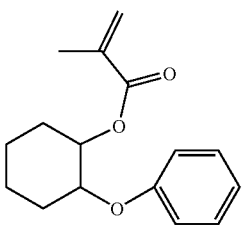

C-15

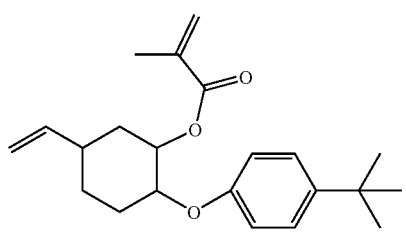

C-16

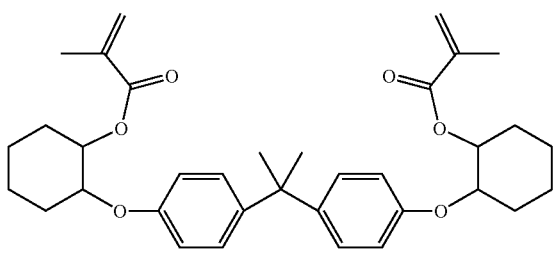

C-17

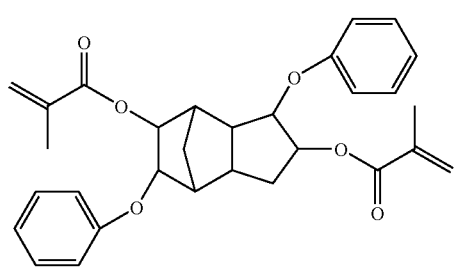

C-18

Exemplary hybrid epoxy-(meth)acrylate thermoset oligomers of the invention, include those where a poly-functional epoxy compound has been partially reacted with a reactive ester such as phenyl methacrylate or 2,2,2-trifluoroethyl acrylate as shown below as C-19 and C-20, respectively.

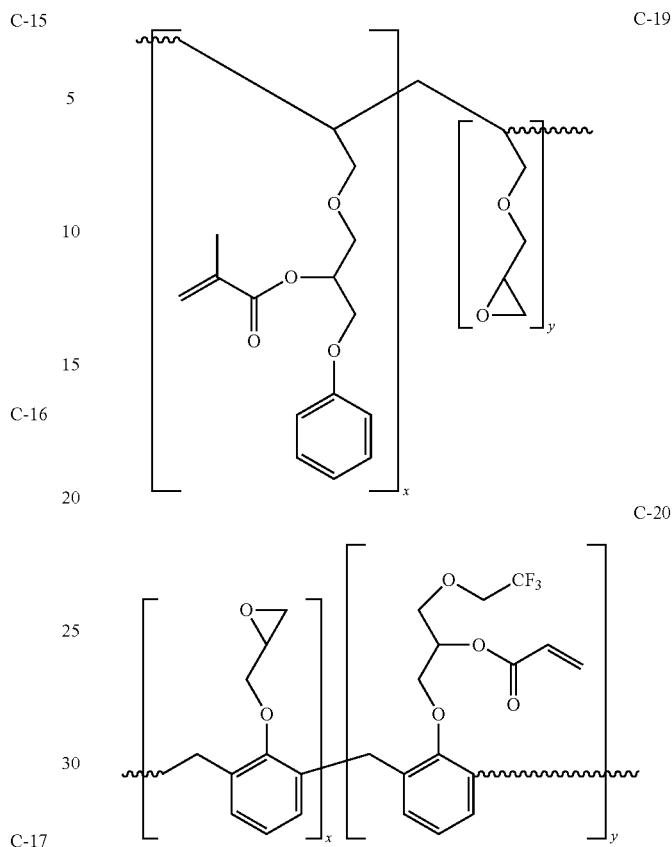

where x and y are independently about 1 to about 10.

The present invention also provides adhesive compositions containing at least one monomer of formula I, II and/or III, and at least one curing initiator.

In some embodiments, the invention monomer is present in the composition from 0.05 weight percent to about 98 weight percent (wt %) based on total weight of the composition. In other embodiments, there is at least one co-monomer typically present in the composition from 0.05 wt % to about 90 wt % based on total weight of the composition. Such comonomers include, for example, acrylates, methacrylates, maleimides, vinyl ethers, vinyl esters, styrenic compounds, allyl functional compounds, olefins, epoxies, oxetanes, benzoxazines, anhydrides, phenyl esters, phenols, and the like.

The at least one curing initiator is typically present in the composition from 0.1 wt % to about 5 wt % based on total weight of the composition, and is typically a free-radical initiator. As used herein, the term "free radical initiator" refers to any chemical species which, upon exposure to sufficient energy (e.g., light, heat, or the like), decomposes into two parts which are uncharged, but which each possesses at least one unpaired electron. Preferred free radical initiators contemplated for use in the practice of the present invention are compounds which decompose (i.e., have a half life in the range of about 10 hours) at temperatures in the range of about 70° C. up to 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methylpropanenitrile), 2,2'-azobis(2-methylbutanenitrile), and 1,1'-azobis(cyclohexanecarbonitrile)), and the like.

The term "free radical initiator" also includes photoinitiators. For example, for invention adhesive compositions that contain a photoinitiator, the curing process can be initiated by UV radiation. In one embodiment, the photoinitiator is present at a concentration of 0.1 wt % to 5 wt % based on the total weight of the organic compounds in the composition (excluding any filler). In a one embodiment, the photoinitiator comprises 0.1 wt % to 3.0 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In certain embodiments, the adhesive compositions of the invention are thermosetting adhesives in which all of the original epoxy functionality has been converted to free radical polymerizable moieties.

In certain other embodiments the original epoxy functionality is only partially converted to free radical polymerizable moieties. This partial conversion is useful for hybrid, or two-stage cures in which the final thermoset adhesive or article is achieved by two independent steps. Thus, an adhesive of the invention can be "b-staged" through an initial cure of either the epoxy or free-radical moiety, followed by a final cure of the remaining functionality. This dual cure property is particularly useful for pre-applied or film-based adhesives. The dual functional monomers are also useful as adhesion promoters at the interface between two different thermoset chemistries. An example of this type of application would be their use as a "tie layer" between a free radical monomer based die attach material and an epoxy mold compound encapsulant.

The invention also provides methods for attaching a first article to a second article using the adhesive compositions described herein. Typically, this method will include a) applying an aliquot of the adhesive composition of the to the first article, second article or both the first and second article; b) bringing the first and second article into intimate contact to form an assembly wherein the first article and the second article are separated only by the adhesive composition applied in step a), and c) curing the adhesive composition.

EXAMPLES

Example 1

Compound C-1

A 250 mL, single neck, round bottom flask was charged with 17.0 g (0.050 mole) of D.E.R. 332 (the diglycidyl ether of bisphenol A), 16.66 g (0.103 mole) of 4-acetoxystyrene, 0.2 g DMAP catalyst, and a stir bar. This mixture was stirred at 85° C. for 60 hours. The mixture was then sparged with clean dry air at this same temperature to remove all volatiles. A total of 33.4 g (100% of theory) of a tacky, red, very viscous liquid was obtained. An FTIR run on this product had strong absorptions at 1738, 1628, 1605, 1505, 1221, 1046, 903, 834, and 734 wave numbers. A TGA (10° C. per minute ramp, air purge) on this compound revealed 1.6% weight loss at 300° C., and a decomposition onset at 430.8° C.

Example 2

Compound C-2

A 250 mL, single neck, round bottom flask was charged with 15.8 g (0.050 mole) of the diglycidyl ether of bisphenol F, 16.66 g (0.103 mole) of 4-acetoxystyrene, 0.2 g DMAP, and 0.064 g BHT. This mixture was stirred at 100° C. for 26 hours. The mixture, which had initially been colorless, had transformed to a viscous brown colored liquid. The crude product was taken up in 150 mL toluene and this solution was passed over 20 g of silica gel. The solvent was removed to yield 29.48 g (93%) of a very viscous, clear, yellow liquid. An FTIR was run on this product and it was found to have strong absorptions at 1738, 1605, 1505, 1453, 1372, 1212, 1098, 1044, 989, 902, 835, and 752 wave numbers. A TGA (10° C. per minute ramp, air purge) was run on this compound and it was found to have 1.1% weight loss at 300° C. and a decomposition onset of 434° C. A DSC (10° C. per minute ramp, air purge) was also run on this compound in the presence of 2% dicumyl peroxide. The catalyzed monomer cured with an onset temperature of 148.8° C., a peak temperature of 160.6° C., and a cure energy of 157.7 J/g.

Example 3

Compound C-3

A 250 ml, single neck, round bottom flask was charged with 10.81 g (0.050 mole) Heloxy 68 (neopentyl glycol diglycidyl ether), 16.66 g (0.103 mole) 4-acetoxystyrene, 0.2 g DMAP, and 0.056 g BHT. This mixture was stirred for 17 hours at 100° C. The mixture was then diluted with 150 mL of toluene and this solution was refluxed for another 9.5 hours. The solution was then refluxed for another 9.5 hours. The solution was passed over 20 g of silica gel and the toluene was removed to yield 24.2 g (89.4%) of a relatively low viscosity red liquid. An FTIR run on this compound revealed strong absorptions at 1738, 1628, 1606, 1510, 1372, 1232, 1114, 1046, 904, and 834 wave numbers. A TGA (10° C. per minute ramp, air purge) showed a 9.2% weight loss at 300° C. and a decomposition onset at 405.8° C. A DSC was also run on this compound (10° C. per minute ramp, air purge) in the presence of 2% dicumyl peroxide. The catalyzed monomer cured with an onset temperature of 175.5° C., a peak temperature of 187.8° C. and a cure energy of 103.4 J/g.

Example 4

Compound C-6

A 250 ml, single neck, round bottom flask was charged with 15.8 g (0.050 mole) bisphenol F diglycidyl ether, 18.5 g (0.110 mole) 2,2,2-trifluoroethyl methacrylate, 0.2 g DMAP, and 0.064 g BHT. This mixture was stirred for 30 hours in an oil bath controlled at 100° C. The mixture was then diluted with 150 mL of toluene. The solution was passed over 20 g of silica gel and the toluene was removed to yield 24.85 g (77.1%) of a moderately viscous, clear, red liquid. An FTIR run on this compound revealed strong absorptions at 1721, 1638, 1510, 1453, 1279, 1240, 1157, 1048, 970, 813, 753, and 666 wave numbers. A TGA (10° C. per minute ramp, air purge) showed a 4.1% weight loss at 300° C. and a decomposition onset at 366.7° C. A DSC was also run on this compound (10° C. per minute ramp, air purge) in the presence of 2% dicumyl peroxide. The catalyzed monomer cured with an onset temperature of 132.1° C., a peak temperature of 144.6° C. and a cure energy of 126.4 J/g. A TMA run on a cured sample of this monomer (ramp at 5° C. per minute) revealed an $\alpha_1$=65.1 ppm/° C., an $\alpha_2$=221.2 ppm/° C., and a $T_g$=40.8° C.

Example 5

Compound C-9

The starting material 4-methacyloxybiphenyl was prepared by charging a 250 mL, 1-neck flask with 34.04 g (0.2 mole) 4-phenylphenol, 30.3 g (0.21 mole) methacrylic anhydride, 100 mL toluene, 0.2 g DMAP, and 0.025 g BHT. This mixture was stirred at 80° C. for 40 hours. The solution was then passed over 20 g of silica gel and the solvent was removed to yield 47.8 g (100% of theory) of a white solid that had a melting point of 111-112.6° C. The FTIR spectrum of this compound showed all of the phenolic —OH had disappeared. It also revealed prominent absorptions at 1731, 1637, 1484, 1320, 1207, 1127, 761, and 696 wave numbers.

A 125 mL single-neck flask was charged with 23.83 g (0.100 mole) of the above compound, 13.7 g (0.120 mole) allylglycidyl ether, 0.2 g DMAP, 0.07 g BHT, and 130 mL toluene. This mixture was stirred at 100° C. for 46 hours. The mix was originally two phases, but became a hazy single phase within the first hour of mixing at temperature. The solution was cooled and then passed over 30 g of silica gel. The solvent was removed to yield 26.1 g (74.0% of theory) of a clear, red, fairly mobile liquid. An FTIR revealed prominent absorptions at 1719, 1637, 1609, 1519, 1485, 1291, 1249, 1154, 1108, 1045, 937, 832, 762, and 696 wave numbers. A DSC was run on this compound in the presence of 2% dicumyl peroxide (10° C. per minute ramp, air purge). A cure was observed to occur at 155.6° C. with an onset temperature of 141.0° C. The cure energy was 150.8 J/g. A TGA was run on the monomer with and without 2% added dicumyl peroxide (10° C. per minute ramp, air purge). The weight loss at 300° C. was 16.9% in the presence of the catalyst and 31.3% without it.

Example 6

Compound C-13

A 250 ml, single neck, round bottom flask was charged with 10.11 g (0.05 mole) 1,4-butanedioldiglycidyl ether, 20.3 g (0.125 mole) phenyl methacrylate, 0.2 g DMAP and 0.054 g BHT. This mixture was stirred at 100° C. for 46 hours. The mixture became a more viscous liquid and turned to a dark brown color as the reaction proceeded. The mix was then dissolved in 150 ml toluene and passed over 20 g of silica. The solvent and excess phenyl methacrylate was removed to yield 22.9 g (87.0% of theory) of a clear, light orange, moderately viscous liquid. An FTIR was run on this compound and major absorptions were found at 1714, 1637, 1599, 1495, 1292, 1242, 1158, 1044, 941, 813, 753, and 691 wave numbers. A TGA run on this material showed 0.2% weight loss at 200° C. and 4.3% weight loss at 300° C. A DSC was run on the monomer in the presence of 2% dicumyl peroxide (10° C. per minute ramp, air purge) that showed a cure maxima at 138.8° C. and an onset at 131.5° C. The cure energy was 157 J/g. A TMA was run (ramp at 5° C. per minute) on a cured pellet of this monomer. The cured thermoset was found to have a $\alpha_1$=60.2 ppm/° C., $\alpha_2$=202.1 ppm/° C., and a glass transition temperature of 7.83° C.

Example 7

Compound C-15

A 100 ml, single neck, round bottom flask was charged with 16.22 g (0.10 mole) phenyl methacrylate, 9.81 g (0.10 mole) cyclohexene oxide, 0.2 g DMAP, and 0.054 g BHT. This mixture was stirred and heated at 100° C. for 90 hours. The crude product was dissolved in 150 mL toluene and then passed over 20 g of silica gel. The solvent was removed to yield 23.24 g (89.3% of theory) of a low viscosity, clear, red liquid. An FTIR run on this liquid revealed strong absorptions at 2940, 1713, 1638, 1599, 1492, 1329, 1292, 1233, 1158, 1027, 942, 809, 752, and 691 wave numbers. A TGA run on this material (10° C. per minute ramp, air purge) showed 0.2% weight loss at 100° C. and 11.2% weight loss at 200° C. A DSC was run on the monomer in the presence of 2% dicumyl peroxide (10° C. per minute ramp, air purge) that showed a cure maxima at 150.5° C. and an onset at 146.8° C. The cure energy was 157 J/g.

What is claimed is:

1. A compound having the formula:

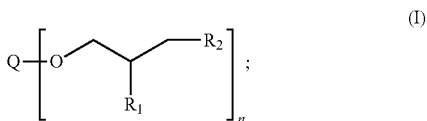

(I)

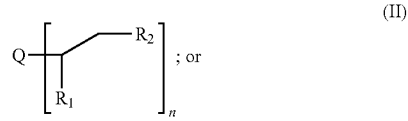

(II)

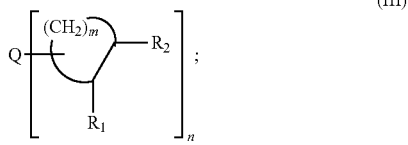

(III)

wherein:
each of $R_1$ and $R_2$ is independently selected from the group consisting of a substituted or unsubstituted acyloxy, cycloacyloxyl, benzoxy, maleimido acyloxy, styryloxy, cinnamyloxy, 2,2,2-trifluoroethoxy, 2-nitroethoxy, 2-cyanoethoxy and acetomethoxy;
Q is a residue of a glycidyl ether epoxy with respect to formula (I), an aliphatic epoxy with respect to formula (II), and a cycloaliphatic epoxy with respect to formula (III);
m is an integer having the value of 3 to 10; and
n is an integer having the value of 1 to about 11,
with the further proviso that:
(a) if $R_1$ is an unsubstituted acyloxy or maleimido acyloxy group, then $R_2$ is a moiety selected from the group consisting of cycloacyloxyl, benzoxy, styryloxy, cinnamyloxy, 2,2,2-trifluoroethoxy, 2-nitroethoxy, 2-cyanoethoxy and acetomethoxy; and
(b) if $R_2$ is an unsubstituted acyloxy or maleimido acyloxy group, then $R_1$ is a moiety selected from the group consisting of cycloacyloxyl, benzoxy, styryloxy, cinnamyloxy, 2,2,2-trifluoroethoxy, 2-nitroethoxy, 2-cyanoethoxy and acetomethoxy.

2. The compound of claim 1, wherein at least one of $R_1$ or $R_2$ is selected from the group consisting of:

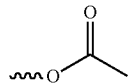

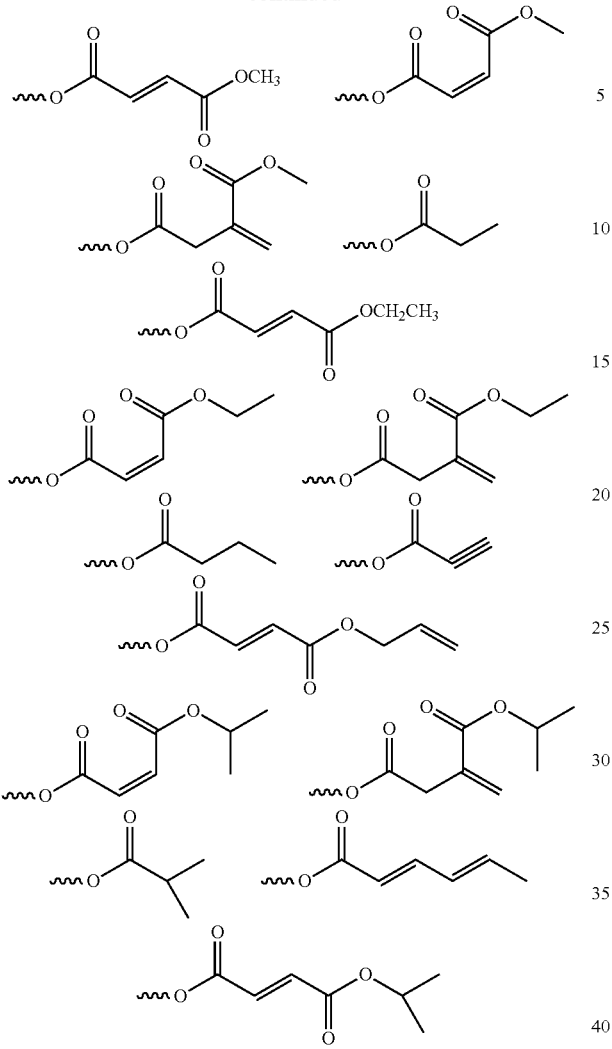
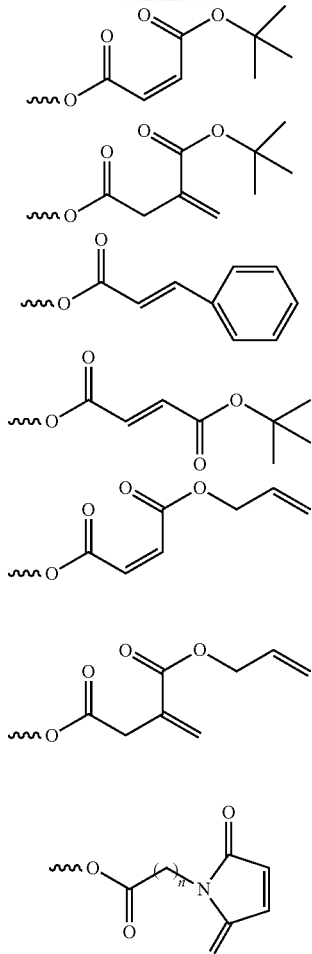
Where: n = 1 to 11
3. A compound selected from the group consisting of:
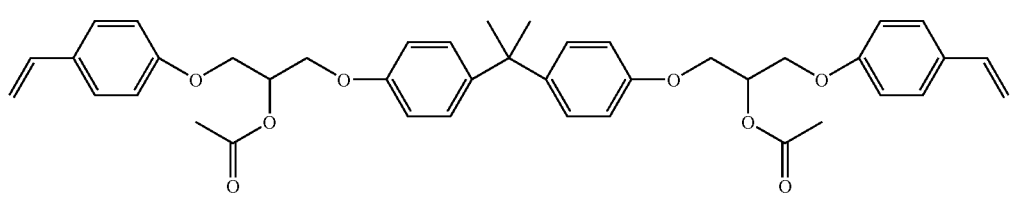
C-1
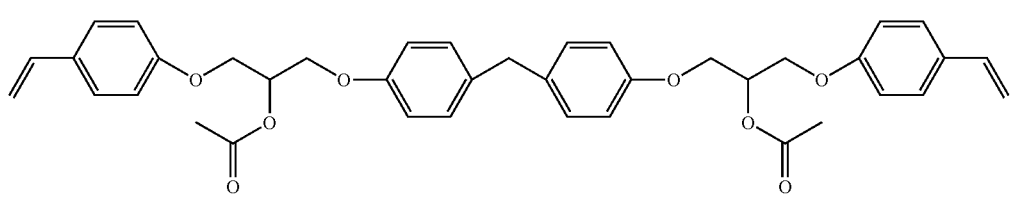
C-2

-continued
C-3
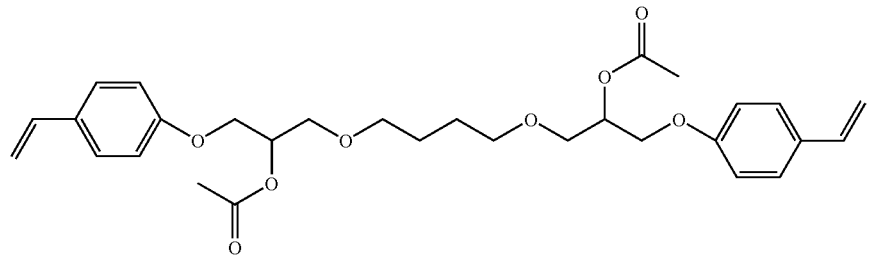
C-4
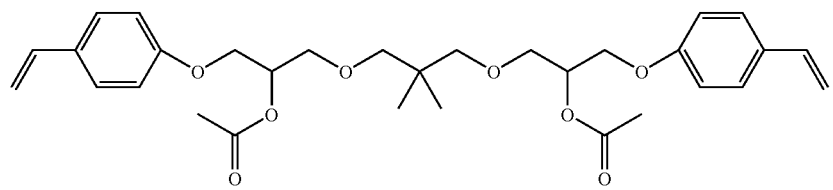
C-5
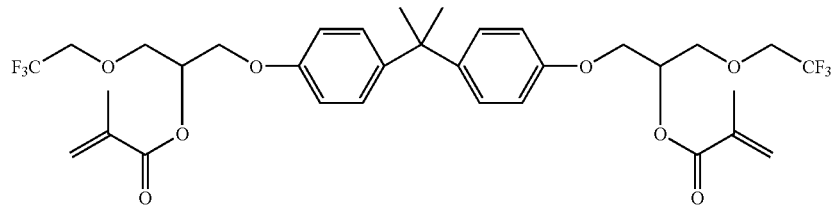
C-6
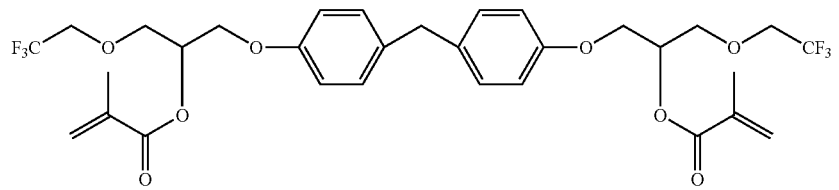
C-7
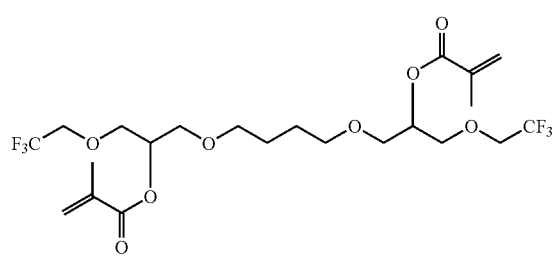
C-8
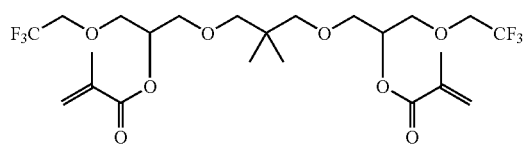
C-9
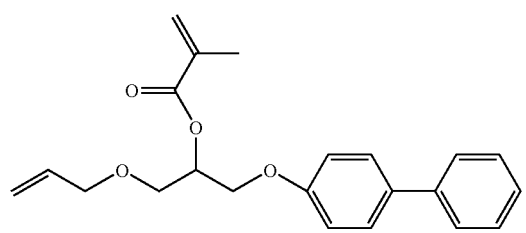
C-10
C-11
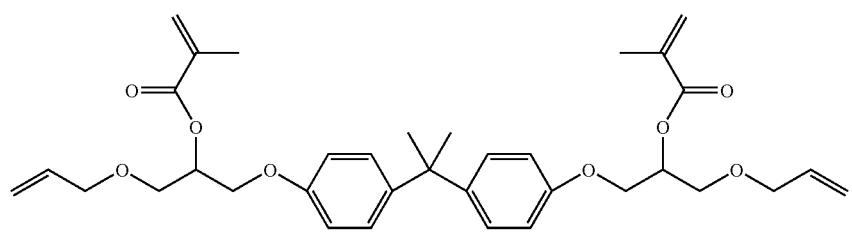

-continued
C-12
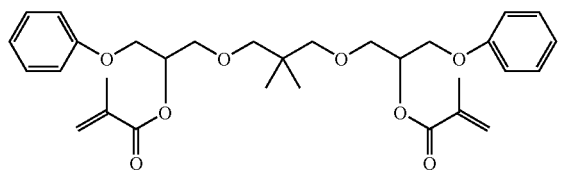
C-13
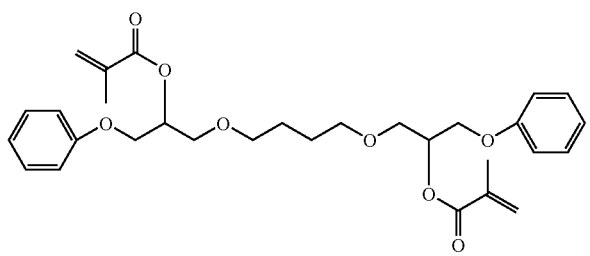
C-14
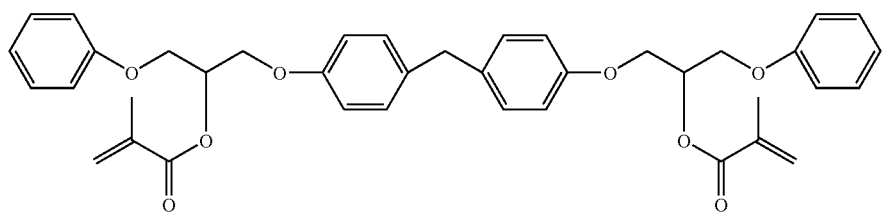
C-15
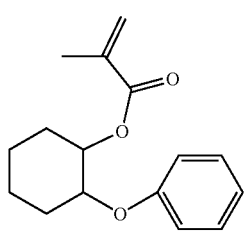
C-16
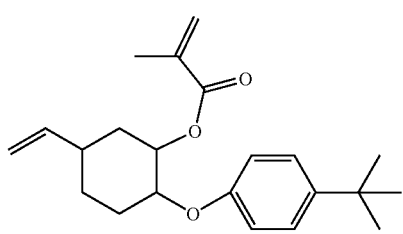
C-17
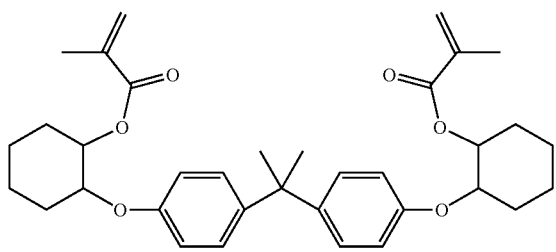
C-18
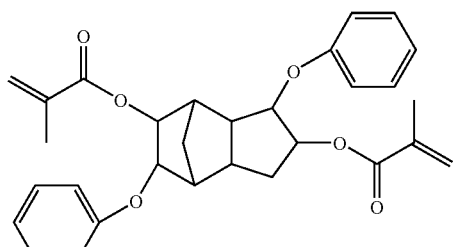
C-19
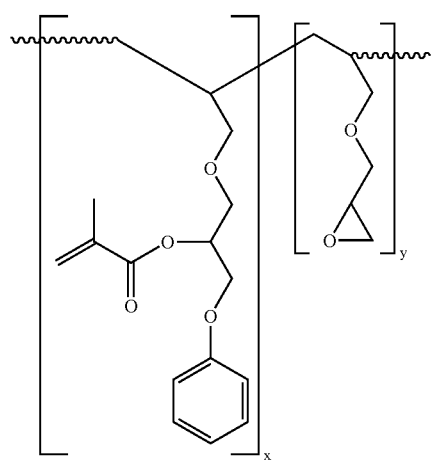
C-20
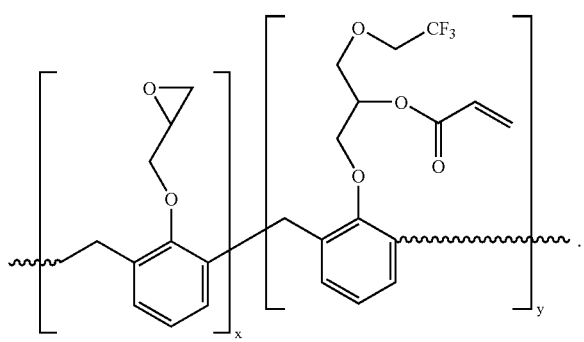

wherein each of x and y is an integer independently having the value of about 1 to about 10.

4. A method for preparing a compound of claim 1, comprising:
   contacting an epoxy with a reactive ester in the presence of a catalyst, wherein a free radical curable monomer is produced,
   thereby preparing a compound of claim 1.

5. The method of claim 4, wherein the epoxy is only partially converted to a free radical polymerizable moiety.

6. The method of claim 4, wherein the catalyst is a basic catalyst.

7. The method of claim 6, wherein the catalyst is selected from the group consisting of 4-(N,N-dimethylamino)pyridine (DMAP), 4-(4-methyl-1-piperidinyl)pyridine (MPP), 1,5-diazabicyclo[4.3.0]non-5-ene (DBN), 1,4-diazabicyclo[2.2.2]octane (DABCO), 1,8-diazabicyclo[5.4.0]undec-7-ene (DBU) and tetrabutylammonium bromide (TBAB).

8. The method of claim 4, wherein the epoxy is a mono-, or bi-functional, or poly-functional glycidyl ether epoxy, cycloaliphatic epoxy or aliphatic epoxy.

9. The method of claim 8, wherein the epoxy is selected from the group consisting of
   a phenyl glycidyl ether;
   a cresyl glycidyl ether;
   a nonylphenyl glycidyl ether;
   a p-tert-butylphenyl glycidyl ether;
   a diglycidyl or polyglycidyl ether of any one of:
      bisphenol A, of bisphenol F, of ethylidenebisphenol, dihydroxydiphenyl ether, bis(4-hydroxyphenyl)sulfone, bis(hydroxyphenyl)sulfide, 1,1-bis(hydroxyphenyl)cyclohexane, 9,19-bis(4-hydroxyphenyl)fluorene, 1,1,1-tris(hydroxyphenyl)ethane, tetrakis(4-hydroxyphenyl)ethane, trihydroxytritylmethane, 4,4'-(1-alpha-methylbenzylidene)bisphenol, 4,4'-dihydroxybenzophenone, dihydroxy naphthalene, 2,2'-dihydroxy-6,6'-dinaphthyl disulfide, or 1,8,9-trihydroxyanthracene, resorcinol, catechol or tetrahydroxydiphenyl sulfide;
   triglycidyl-p-aminophenol;
   N,N,N',N'-tetraglycidyl-4,4'-diphenylmethane;
   triglycidyl isocyanurate;
   a glycidyl ether of a cresol formaldehyde condensate;
   a glycidyl ether of a phenol formaldehyde condensate;
   a glycidyl ether of a cresol dicyclopentadiene addition compound;
   a glycidyl ether of a phenol dicyclopentadiene addition compound;
   a diglycidyl ether of 1,4 butanediol;
   a diglycidyl ether of diethylene glycol;
   a diglycidyl ether of neopentyl glycol;
   a diglycidyl ether of cyclohexane dimethanol;
   a diglycidyl ether of tricyclodecane dimethanol;
   a trimethyolethane triglycidyl ether;
   a trimethyol propane triglycidyl ether;
   a glycidyl ether of a polyglycol;
   a polyglycidyl ether of castor oil;
   a polyoxypropylene diglycidyl ether and
   a glycidyl derivative of an aromatic amine.

10. An adhesive composition comprising:
    at least one compound of claim 1; and
    at least one curing initiator.

11. The adhesive composition of claim 10 comprising:
    0.05 weight percent to about 98 weight percent of a monomer compound of claim 1;
    optionally 0.05 weight percent to about 98 weight percent of at least one co-monomer; and
    0.1 weight percent to about 5 weight percent of a curing initiator.

12. The adhesive composition of claim 10, wherein the curing initiator is selected from the group consisting of a free-radical initiator, photoinitiator or a combination of a free-radical initiator and a photoinitiator.

13. The adhesive composition of claim 12, wherein the curing initiator is selected from the group consisting of dicumyl peroxide, dibenzoyl peroxide, 2-utanone peroxide, tert-butyl perbenzoate, di-tert-butyl peroxide, 2,5-bis(tert-butylperoxy)-2,5-dimethylhexane, bis(tert-butyl peroxyisopropyl)benzene, tert-butyl hydroperoxide, 2,2'-azobis(2-methyl-propanenitrile), 2,2'-azobis(2-methylbutanenitrile), a 1,1'-azobis(cyclohexanecarbonitrile), a benzoin derivative, a benzilketal, an α,α-dialkoxyacetophenone, an α-hydroxyalkylphenone, an α-aminoalkylphenone, an acylphosphine oxide, a titanocene compound, a benzophenone, an amine, Michler's ketone and a combination thereof.

14. The adhesive composition of claim 11, wherein the comonomer is selected from the group consisting of an acrylate, a methacrylate, a maleimide, a vinyl ether, a vinyl esters, a styrenic compound, an allyl functional compound, an olefin, an epoxy, an oxetane, a benzoxazine, an anhydride, a phenyl ester and a phenol.

15. An adhesive composition comprising:
    a monomer compound of claim 5;
    optionally a comonomer; and
    a curing initiator.

16. A method for adhesively attaching a first article to a second article comprising:
    a. applying an aliquot of the adhesive composition of claim 10 to the first article, the second article or both the first article and the second article;
    b. bringing the first article and the second article into intimate contact to form an assembly wherein the first article and the second article are separated only by the adhesive composition applied in step a); and
    c. curing the adhesive composition.

17. A method for adhesively attaching a first article to a second article comprising:
    a. applying an aliquot of the adhesive composition of claim 15 to the first article, the second article or both the first article and the second article;
    b. bringing the first article and the second article into intimate contact to form an assembly wherein the first article and the second article are separated only by the adhesive composition applied in step a);
    c. curing either an epoxy or free-radical moiety of the monomer, thereby producing a cured moiety and an uncured moiety of the adhesive composition; and
    d. thereafter curing the uncured moiety.

18. A method for preparing a compound comprising:
    contacting an epoxy with a reactive ester in the presence of a catalyst, wherein a free radical curable monomer is produced, wherein the epoxy is only partially converted to a free radical polymerizable moiety,
    thereby preparing the compound having the formula selected from the group consisting of

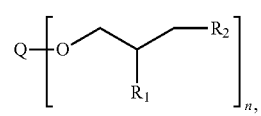

(I)

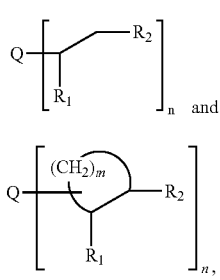

wherein:
each of $R_1$ and $R_2$ is independently selected from the group consisting of a substituted or an unsubstituted acyloxy, cycloacyloxyl, benzoxy, acryloxy, methacryloxy, maleimido acyloxy, styryloxy, cinnamyloxy, 2,2,2-trifluoroethoxy, 2-nitroethoxy, 2-cyanoethoxy, acetomethoxy and aryloxy;

Q is a residue of a glycidyl ether epoxy with respect to formula (I), an aliphatic epoxy with respect to formula (II), and a cycloaliphatic epoxy with respect to formula (III);

m is an integer having the value of 3 to 10; and n is an integer having the value of 1 to about 11.

19. An adhesive composition comprising:
at least one compound of claim 3; and
at least one curing initiator.

20. The adhesive composition of claim 19 comprising:
0.05 weight percent to about 98 weight percent of a monomer compound of claim 3;
optionally 0.05 weight percent to about 98 weight percent of at least one co-monomer; and
0.1 weight percent to about 5 weight percent of a curing initiator.

21. The adhesive composition of claim 20, wherein the comonomer is selected from the group consisting of an acrylate, a methacrylate, a maleimide, a vinyl ether, a vinyl esters, a styrenic compound, an allyl functional compound, an olefin, an epoxy, an oxetane, a benzoxazine, an anhydride, a phenyl ester and a phenol.

22. The adhesive composition of claim 3, wherein the curing initiator is selected from the group consisting of a free-radical initiator, photoinitiator or a combination of a free-radical initiator and a photoinitiator.

23. The adhesive composition of claim 20, wherein the curing initiator is selected from the group consisting of dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, tert-butyl hydroperoxide), 2,2'-azobis(2-methyl-propanenitrile), 2,2'-azobis(2-methylbutanenitrile), a 1,1'-azobis(cyclohexanecarbonitrile), a benzoin derivative, a benzilketal, an α,α-dialkoxyacetophenone, an α-hydroxyalkylphenone, an α-aminoalkylphenone, an acylphosphine oxide, a titanocene compound, a benzophenone, an amine, Michler's ketone, and a combination thereof.

24. A method for adhesively attaching a first article to a second article comprising:
a. applying an aliquot of the adhesive composition of claim 19 to the first article, the second article or both the first article and the second article;
b. bringing the first article and the second article into intimate contact to form an assembly wherein the first article and the second article are separated only by the adhesive composition applied in step a); and
c. curing the adhesive composition.

* * * * *